US006333359B1

(12) United States Patent
Guillet et al.

(10) Patent No.: US 6,333,359 B1
(45) Date of Patent: Dec. 25, 2001

(54) REGULATION OF CELLULAR APOPTOSIS USING MODULATORS OF β-AR RECEPTORS

(75) Inventors: Jean-Gérard Guillet, Vanves; Claudine Andre, Fontenay sous Bois; Pascale Briand, Paris, all of (FR)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 0 days.

(21) Appl. No.: 09/509,194

(22) PCT Filed: Sep. 22, 1998

(86) PCT No.: PCT/FR98/02030

§ 371 Date: Sep. 23, 1997

§ 102(e) Date: Sep. 23, 1997

(87) PCT Pub. No.: WO99/15158

PCT Pub. Date: Apr. 1, 1999

(30) Foreign Application Priority Data

Sep. 23, 1997 (FR) .................................................. 97 11820

(51) Int. Cl.[7] ...................... A61K 31/135; A61K 31/445; A61K 31/27; A61K 31/045
(52) U.S. Cl. .......................... 514/653; 514/318; 514/481; 514/724
(58) Field of Search .................................... 514/653, 724, 514/318, 481

(56) References Cited

PUBLICATIONS

Heiko Mühl et al., "Apoptosis is triggered by the cyclic AMP signalling pathway in renal mesangial cells", Mar. 18, 1996 Federation of European Biochemical Societies, *FEBS Letters*, vol. 382, pp. 271–275.

Y. Shizukuda et al., "$\beta_2$–Adrenergic Stimulation Induces Cardiocyte Apoptosis Which Is Not Mediated by an Increase in Heart Rate", 47th Annual Scientific Session of the American College of Cardiology, Atlanta, Georgia, Mar. 29–Apr. 1, 1998, *Journal of the American College of Cardiology*, vol. 31, (2 Suppl. A), abstract.

Yukitaka Shizukuda et al., "Continuous Beta–Adrenergic Stimulation Induces Apoptosis in Rat Myocardium", 70th Scientific Sessions of the American Heart Association, Orlando, Florida, Nov. 9–12, 1997, *Circulation*, vol. 96 (8 Suppl)., pp. 1743–1744, abstract.

Kazuko Suzuki et al., "Modulation of Thymocyte Apoptosis by Isoproterenol and Prostaglandin $E_2$", 1991 *Cellular Immunology*, vol. 134, pp. 235–240.

Can–Fang Wu et al., "Atrial Natriuretic Peptide Induces Apoptosis in Neonatal Rat Cardiac Myocytes", Jun. 6, 1997, *The Journal of Biological Chemistry*, vol. 272, No. 23, pp. 14860–14866.

Tian–Li Yue et al., "Possible Involvement of Stress–Activated Protein Kinase Signaling Pathway and Fas Receptor Expression in Prevention of Ischemia/Reperfusion–Induced Cardiomyocyte Apoptosis by Carvedilol", Feb. 9, 1998, vol. 82, *Cir. Res.*, pp. 166–174.

You–Qing Zhang et al., "Norepinephrine Reverses the Effects of Activin A on DNA Syntheisi and Apoptosis in Cultured Rat hepatocytes", Feb. 1999 *Hepatology*, vol. 23, No. 2, pp. 288–293.

Yuan Zhu et al., "Stimulation of $\beta_2$–Adrenoceptors Inhibits Apoptosis in Rat Brain After Transient Forebrain Ischemia", 1998 *Journal of Cerebral Blood Flow and Metabolism*, vol. 18, No. 9, pp. 1032–1039.

Kim L. Anderson et al., "Intracellular Signaling Pathways Involved in the Induction of Apoptosis in Immature Thymic T Lymphocytes", *J. Immunol*, Jun. 1, 1996, vol. 156, pp. 4083–4091.

Claudine Andre et al., "Transgenic mice carrying the human $\beta_2$–adrenergic receptor gene with its own promoter overexpress $\beta_2$–adrenergic receptors in liver," Oct. 15, 1996, *Eur. J. Biochem.*, vol. 241, No. 2, pp. 417–424.

Catherine Communal et al., "The β–Adrenergic Pathway Mediates Norepinephrine–Stimulated Apoptosis in vitro in Adult Ray Cardiac Myocytes", Oct. 21, 1997, *Circulation*, vol. 96 (8 Suppl.), abstract.

Giora Z. Feuerstein et al., "Apoptosis in cardiac health and disease", *Expert Opinion on Investigational Drugs*, vol. 5, No. 10, pp. 1391–1398.

P. Moreau et al., "Modulation of Apoptotic Activity by Antihypertensive Treatments in Small Arteries", , Annual Meeting of the Canadian Society For Clinical Investigation, The Royal College of Physicians and Surgeons of Canada and Participating Societies, Vancouver, British Columbia, Canada, Sep., 1997, *Clinical and Investigative Medicine*, vol. 20, abstract.

M. Moriyama et al., "Detection of Intrahepatic fFs Antigen In Hepatitis C Patients", *Gastroenterology*, vol. 10, (4 Suppl.), May, 1996, abstract.

Zhu et al., "Stimulation of .beta.2–adrenoceptors inhibits apoptosis in rat brain after transient forebrain ischemia", J. Cereb. Blood Flow Metab. (1998), 18(0), 1032–1039.*

* cited by examiner

*Primary Examiner*—Kevin E. Weddington
(74) *Attorney, Agent, or Firm*—Morgan, Lewis & Bockius LLP

(57) ABSTRACT

The invention concerns the use of β2-adrenergic modulators for regulating cellular apoptosis.

6 Claims, 4 Drawing Sheets

REGULATION OF CELLULAR APOPTOSIS USING MODULATORS OF β-AR RECEPTORS

Figure 1:
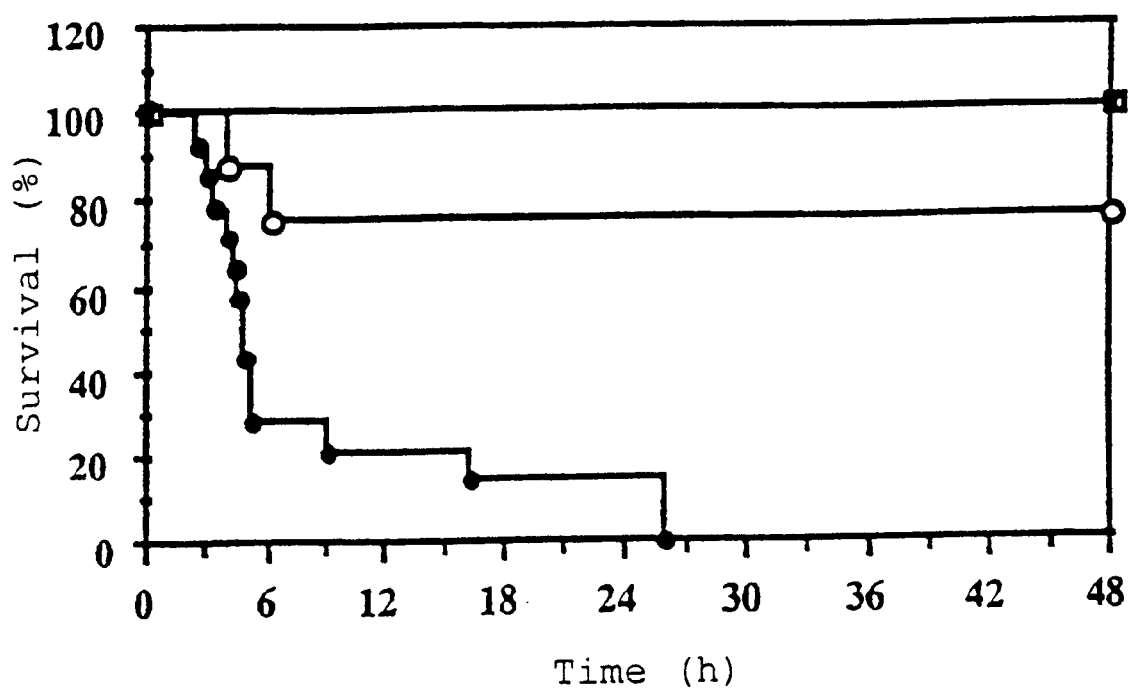

The present invention relates to the use of β2-adrenergic receptor (β2-AR) modulators for the treatment of pathologies associated with a deregulation of apoptosis.

The term "apoptosis" denotes a particular form of cell death which depends on a genetically programmed process. Apoptosis is a physiological mechanism which occurs normally during the development and life of an organism. It is, inter alia, involved in the morphological changes of organs during ontogenesis, the regulation of the number of cells in tissues, the removal of certain sub-populations of lymphocytes in the regulation of the immune system, and the removal of abnormal cells.

Certain diseases are associated with a deregulation of apoptosis. If this is abnormally increased, it leads to excessive cell death (for example in the case of hepatitis, cardiac ischemia, neurodegenerative diseases and AIDS). If, on the other hand, it is insufficient, it allows the survival and proliferation of undesirable cells (for example in the case of carcinogenesis, auto-immune diseases and certain viral infections).

Cell death brought about by apoptosis results from the activation of endogenous endonucleases which destroy the cellular DNA; various factors resulting in this activation have been described. However, the mechanisms governing the mode of action of these factors are still poorly understood.

Two proteins, TNF-α and the Fas ligand [ITOH et al., Cell, 66, pp. 233–240, (1991); OEHM et al., J. Biol. Chem., 267, pp. 10709–10715, (1992)] play a particularly important role in triggering apoptosis processes in many cells. These proteins interact with their respective receptors, TNFR [or TNF-αr] and Fas [or FasAg, CD95, APO-1], at the cell surface. It has been found that the expression of these proteins and/or of their membrane receptors is impaired in certain pathologies associated with a deregulation of apoptosis; for example, in hepatitis, an increase in the expression of TNF-α and TNFR has been observed [SPENGLER et al., Cytokine, 8(11), pp. 864–872, (1996)] and likewise for the expression of the Fas receptors [HIRAMATSU et al., Hepatology, 19, pp. 1354–1350, (1994)]; [MOCHIZUKI et al., J. Hepatology, 24, pp. 1–7, (1996)], which is, in contrast, reduced in the case of hepatocarcinomas [HIGAKI et al., Am. J. Pathol., 149, pp. 429–437, (1996)].

Anti-Fas antibodies having an activity similar to that of FasL are used in experimental models of apoptosis. Injection of these antibodies into mice brings about a fulminant hepatitis due to a massive apoptosis of the hepatocytes, leading to the death of the mice within hours of the injection [OGASAWARA et al., Nature, 364, pp. 806–809, (1993); NAGATA, Prog. Mol. Subcell. Biol., 16, pp. 87–103, (1996)].

Various in vivo inhibitory factors of apoptosis have been demonstrated. It has been observed, for example, that transgenic mice expressing the human Bcl-2 protein [LACRONIQUE et al., Nature Medecine, 2, pp. 80–86, (1996); RODRIGUEZ et al., J. Exp. Med., 183, pp. 1031–1036, (1996)], the T antigen of SV40 [ROUQUET et al., Oncogene, 11, pp. 1061–1067, (1995)], and mice to which protease inhibitors of ICE (interleukin 1β converting enzyme) type had been administered [ROUQUET et al., Curr. Biol., 6, pp. 1192–1195, (1996); RODRIGUEZ et al., J. Exp. Med., 184, pp. 2067–2071, (1996)], or an immunomodulator, linomide [REDONDO et al., J. Clin. Invest., 98, pp. 1245–1252, (1996)], were protected against the hepatic apoptosis induced experimentally with anti-Fas antibodies.

Moreover, the team of the Inventors has previously obtained a transgenic mouse, named F28, which expresses functional human β2-adrenergic receptors (Hβ2-ARs) [ANDRE et al., Eur. J. Biochem., 241, pp. 417–424, (1996)]. In the F28 mouse, the Hβ2-ARs are expressed in the muscle, the heart, the brain, the lungs and, especially, in the liver, in which the level of expression is very high. The expression of the β2-ARs in the liver of the F28 mice is closer to that observed in man than to that observed in normal mice.

The Inventors have now observed that when anti-Fas antibodies are administered to transgenic F28 mice, these mice survive this administration, and that their liver shows few apoptotic foci, whereas in normal mice, anti-Fas antibodies administered under the same conditions bring about a massive apoptosis of the hepatocytes, and the death of the animals.

The Inventors have thus put forward the hypothesis of a relationship between the increase in the number of β2-ARs in the liver cells of F28 mice, and the resistance of these cells to apoptosis, and have investigated whether or not this resistance could effectively result in an increase in the hepatic β2-adrenergic activity.

Several types of β-adrenergic receptor are known, and have been detected in greater or lesser amounts in various tissues of the body. The β1-adrenergic receptors (β1-ARs) and/or β2-adrenergic receptors (β2-ARs) are present in many tissues such as, for example, heart, kidney, lung, liver, brain, adipose tissue, smooth muscle, striated muscle, the cells of the immune system, etc. The β3-adrenergic receptors (or β3-ARs), which are present in smaller number than the above receptors, have been detected in the colon, the heart, the kidneys, the lungs, the liver, the brain, muscle and in particular in adipose tissue. A fourth type of β-AR has been described recently in the human heart [KAUMANN and MOLENAAR, Naunyn-Schmiedeberg's Arch. Pharmacol., 355(6), pp. 667–681, (1997), KAUMANN and LYNHAM, Br. J. Pharmacol., 120(7), pp. 1187–1189, (1997)].

The β-adrenergic receptors intervene in stimulation of the cAMP signaling pathway. According to observations carried out in vitro on various types of cell, it appears that the activation of adenylate cyclase and/or the stimulation of the cyclic AMP (cAMP) signaling pathway have variable effects on apoptosis; for example, apoptosis is stimulated in the thymocytes [KIZAKI et al., Cytokine, 5, pp. 342–347, (1993); MENTZ et al., Eur. J. Immunol., 25, pp. 1798–1801, (1995)], in granular cells [AHARONI et al., Exp. Cell. Res., 218, pp. 271–282, (1995)] and in B cells [LOMO et al., J. Immunol., 154, pp. 1634–1643, (1995); BAIXERAS et al., Scand. J. Immunol., 43, pp. 406–412, (1996)], whereas it is inhibited in T-cell hybridomas [LEE et al., J. Immunol., 151, pp. 5208–5217, (1993); HOSHI et al., Int. Immunol., 6, pp. 1081–1089, (1994)], human neutrophils [ROSSI et al., Biochem. Biophys. Res. Commun., 217, pp. 892–899, (1995)], MCF-7 mammary carcinoma cells [BOE et al., Br. J. Cancer, 72, pp. 1151–1159, (1995)] and cells derived from the spinal cord [BERRIDGE et al., Exp. Hematol., 21, pp. 269–276, (1993)].

In order to determine the possible role of the hepatic β2-adrenergic activity in the resistance to apoptosis, the Inventors administered an agonist specific for the β2-ARs to normal mice, and found that they survived the injection of anti-Fas antibodies, and were protected against the hepatic apoptosis induced by these antibodies. They also found, on the other hand, that the administration to mice of a β2-AR antagonist inhibited the resistance to apoptosis of F28 mice, or that of normal mice treated with the β2-AR agonist.

These results thus show that β2-adrenergic regulation plays a major role in the physiological control of the apoptosis process in vivo.

A subject of the present invention is the use of a β2-adrenergic modulator to obtain a medicinal product for regulating cell apoptosis.

The β2-adrenergic activity modulators which can be used in accordance with the present invention comprise β-AR agonists and antagonists which are active on the β2-ARs; it is possible, for example, to use isoproterenol as an agonist, or propranolol as an antagonist.

Advantageously, modulators that are specific for the β2-AR receptors can be used. Agonists that are specific for the β2-ARs are, for example, clenbuterol, salbutamol and procaterol; antagonists that are specific for the β2-ARs are, for example, ICI 118,551 and butoxamine [BILSKI et al., Br. J. Pharmacol., 69, 292P, (1980); DOOLEY and BITTIGER, J. Pharmacol. Meth., 18, pp. 131–136, (1987); STROSBERG, Recombinant Cell Surface Receptors: Focal Point for Therapeutic Intervention, ed. M. Y. Browne, 57–76 (1996), R. G. Landes Company].

Depending on the type of tissue in which it is desired to regulate the apoptosis, and depending on the type of regulation which it is desired to obtain, i.e. a positive regulation leading to an increase in apoptosis, or a negative regulation leading to a decrease in apoptosis, a β2-AR agonist or antagonist will be chosen.

For example:

In the liver, to inhibit cell apoptosis, for example in the context of treating hepatitis, a β2-AR agonist will be used; in contrast, if it is desired to stimulate apoptosis, for example to destroy cancer cells, a β2-AR antagonist will be used.

In the lung, if it is desired, for example, to stimulate the apoptosis of cancer cells in the case of adenocarcinomas, a β2-AR antagonist will be used.

In the heart, to inhibit cell apoptosis in the context of treating cardiac ischemias, a β2-AR agonist will be used.

In the brain, it will be possible via the same approach to reduce the excessive apoptosis observed in neurodegenerative diseases, or, in contrast, to stimulate apoptosis in the case of cancers.

The present invention will be understood more clearly with the aid of the rest of the description which follows, which refers to non-limiting examples illustrating the demonstration of the role of β2-ARs in the prevention of hepatic apoptosis, and the use of β2-AR agonists to inhibit this apoptosis.

EXAMPLE 1

Demonstration of the Resistance of F28 Mice to Hepatic Apoptosis and of the Protective Effect of Clenbuterol In a first series of experiments, carried out on groups of 3 to 4 animals, 12 transgenic F28 mice (described by ANDRE et al., [Eur. J. Biochem., 241, pp. 417–424 (1996)], and 10 C57B1/6 control mice (supplied by IFFA CREDO Lyon, France) received, via intravenous injection, 15 μg of an anti-Fas monoclonal antibody (Jo2 antibody; PHARMINGEN) diluted in 200 μl of physiological saline.

In a second series of experiments, also carried out on groups of 3 to 4 animals, 12 F28 mice and 10 C57B1/6 mice received a pretreatment with clenbuterol, administered orally (by addition of 1.3 mg/l to the drinking water) 17 hours before the intravenous injection of the anti-Fas monoclonal antibody.

The percentage of surviving mice in each batch, as a function of time (in hours) after the injection of the anti-Fas monoclonal antibody, is illustrated in FIG. 1.

Key to FIG. 1:

C57B1/6 mice not treated with clenbuterol=●
C57B1/6 mice treated with clenbuterol=○
F28 mice not treated with clenbuterol=□
F28 mice treated with clenbuterol=✖.

These results show that in the absence of pretreatment with clenbuterol, all of the F28 mice survived the injection of the anti-Fas antibody, whereas most of the control mice were dead within 5 hours of the injection, and none survived longer than 24 hours.

After treatment with clenbuterol, most of the control mice survive the injection of the anti-Fas antibody; this treatment does not modify the survival of the F28 mice.

In each of the groups, the livers of a number of animals were removed to carry out a histological study. In the case of the animals not treated with clenbuterol, hemorrhagic lesions and a massive apoptosis are observed in the control mice; in the F28 mice, only a few rare apoptotic foci are observed. In the case of the animals treated with clenbuterol, far fewer apoptotic foci are observed in the treated control mice than in the untreated control mice. No apoptotic lesions are visible in the treated F28 mice.

EXAMPLE 2

Inhibition with Propranolol of the Protection Conferred by Clenbuterol—Demonstration of a Dose-Dependent Effect of Clenbuterol In order to confirm that the protection conferred by clenbuterol did indeed involve the β2-ARs, experiments were carried out in the presence of the β-adrenergic antagonist, propranolol.

C57BL/6 mice divided into 5 batches of 3 received the following treatments:

Batch 1: Intravenous injection of 15 μg of anti-Fas Jo2 monoclonal antibodies, without pretreatment;

Batch 2: Intravenous injection of 15 μg of anti-Fas Jo2 monoclonal antibodies, after 18 hours of treatment with 1.3 mg/l of clenbuterol;

Batch 3: Intravenous injection of 15 μg of anti-Fas Jo2 monoclonal antibodies, after a pretreatment for 48 hours with 7 mg/l of propranolol and 17 hours with 7 mg/l of propranolol plus 1.3 mg/l of clenbuterol;

Batch 4: Injection of anti-Fas Jo2 monoclonal antibodies, after treatment for 18 hours with 2.6 mg/l of clenbuterol;

Batch 5: Injection of anti-Fas Jo2 monoclonal antibodies, after a pretreatment for 48 hours with 7 mg/l of propranolol and 18 hours with 7 mg/l of propranolol plus 2.6 mg/l of clenbuterol.

The injection of the anti-Fas monoclonal antibody and the pretreatment with clenbuterol are carried out as described for Example 1 above. The propranolol is administered, like the clenbuterol, orally by addition to the drinking water.

Figure 2A:
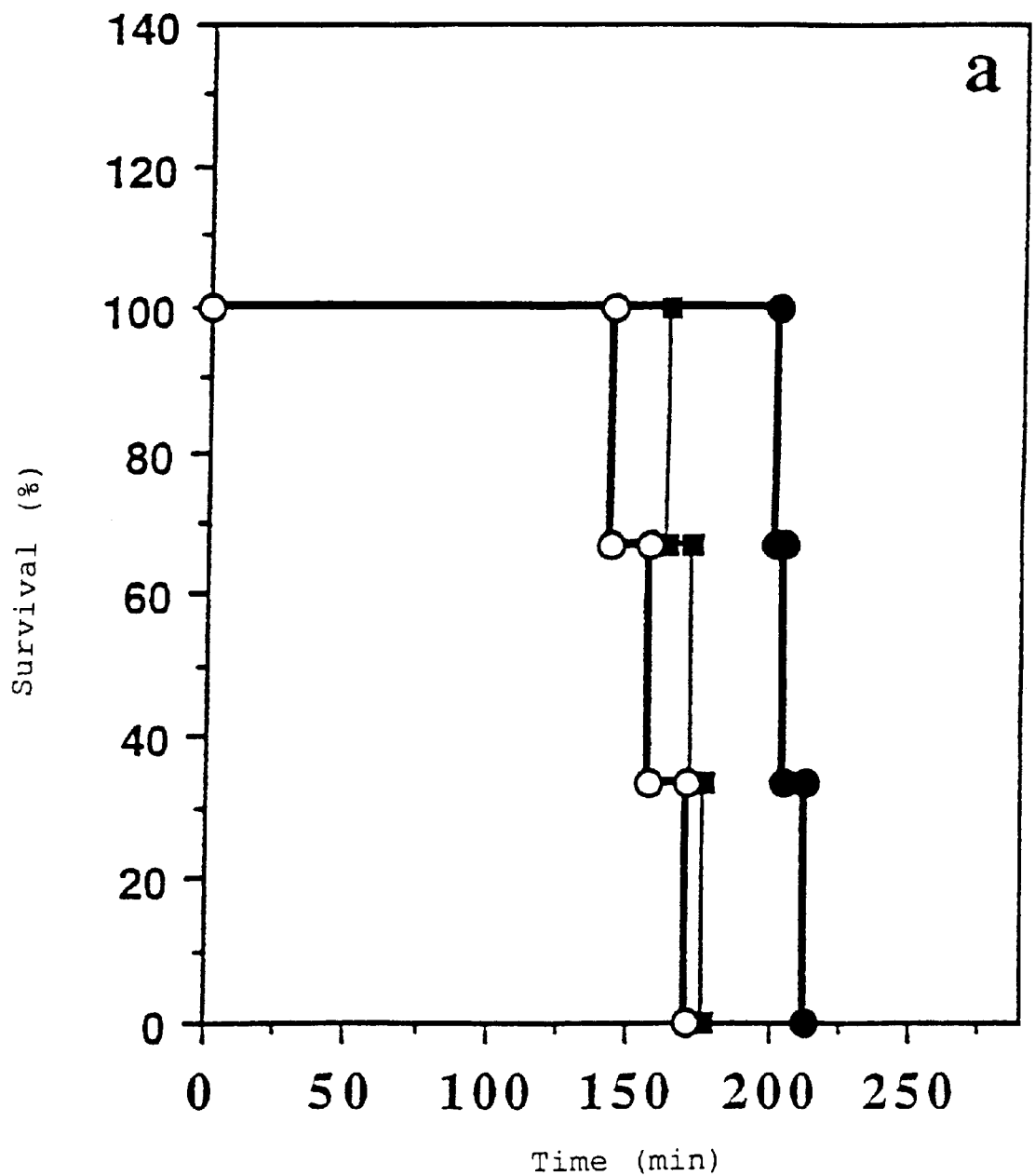
Figure 2B:
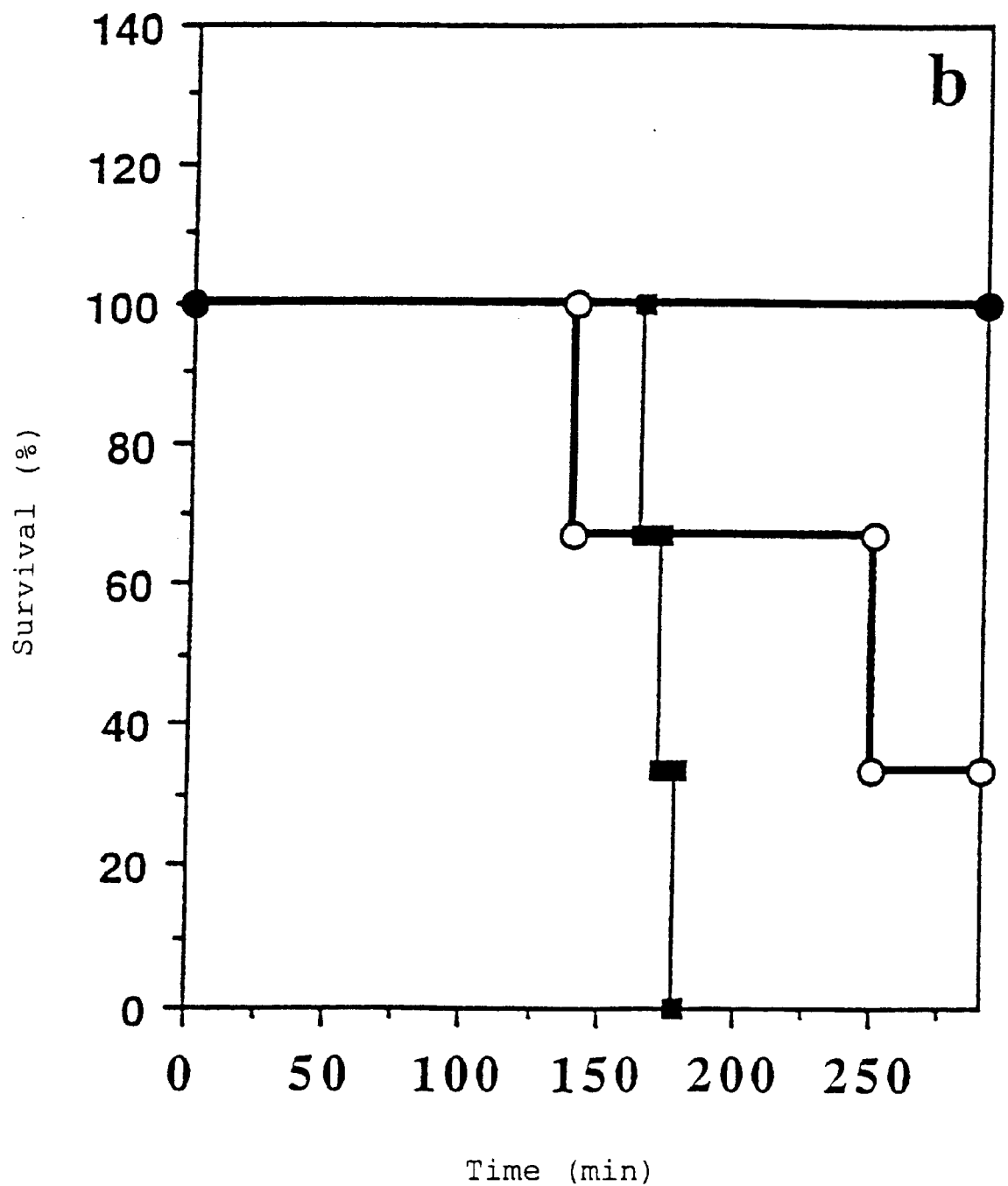

The percentage of surviving mice in each batch, as a function of time (in minutes) after the injection of the anti-Fas monoclonal antibody, is illustrated by FIGS. 2a and 2b.

Key to FIG. 2a:

Batch 1: ■
Batch 2: ●
Batch 3: ○

Key to FIG. 2b:

Batch 1: ■

Batch 4: ●

Batch 5: ○

These results show that the protection conferred by clenbuterol can be inhibited by propranolol (totally for a clenbuterol dose of 1.3 mg/l, and partially for a clenbuterol dose of 2.6 mg/l).

In addition, comparison of the results of FIG. 2a with those of FIG. 2b shows that the protection conferred by clenbuterol is dose-dependent.

EXAMPLE 3

Demonstration of a Dose-Dependent Protective Effect of Salbutamol

C57B1/6 mice received a treatment with salbutamol, administered orally (by addition of 1.4 mg/l or 2.1 mg/l to the drinking water), 17 hours before the intravenous injection of the anti-Fas Jo2 monoclonal antibody, according to the protocol described in Example 1.

Figure 3:
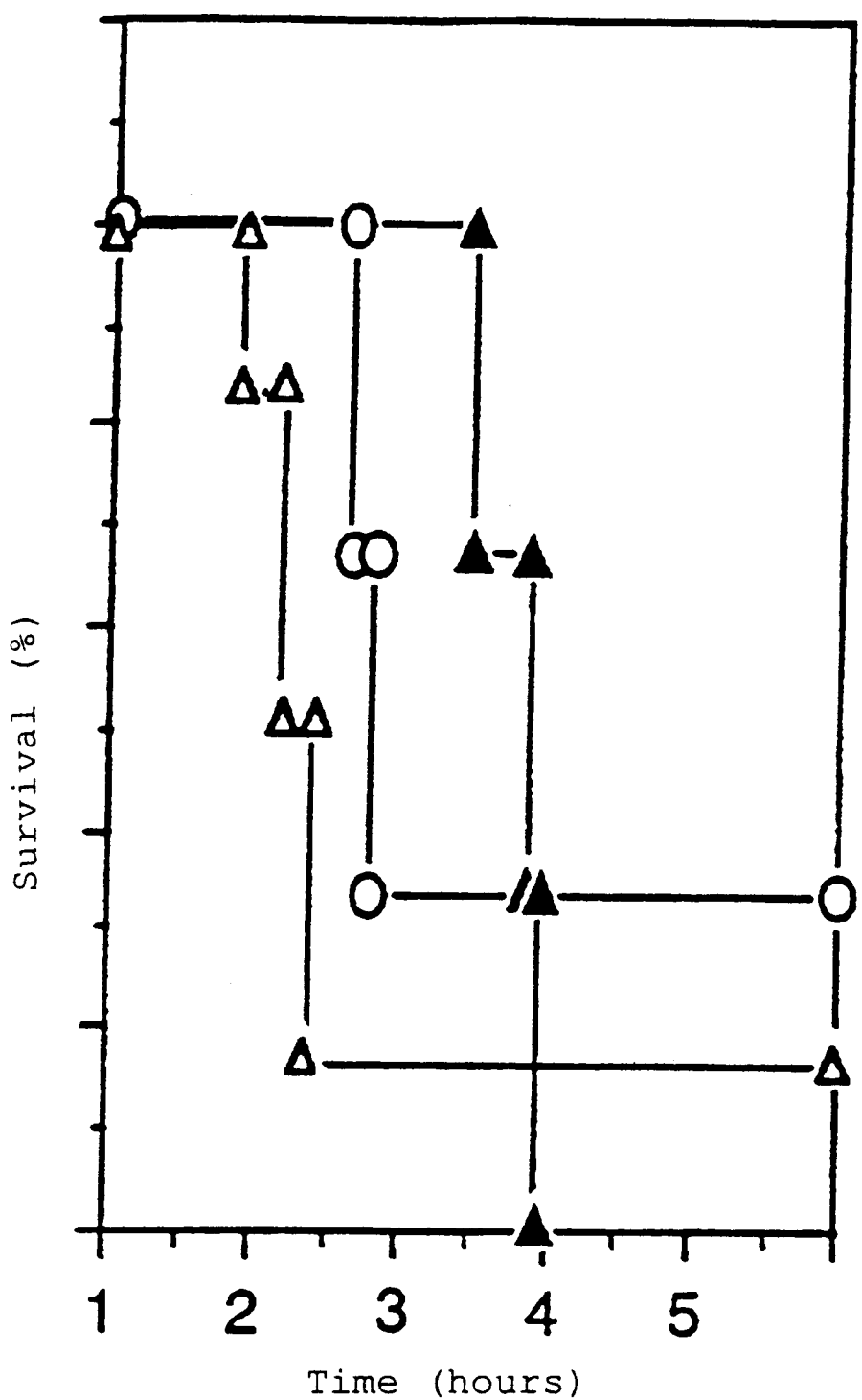

The percentage of surviving mice in each batch, as a function of time (in hours) after the injection of the anti-Fas monoclonal antibody, is illustrated by FIG. 3.

Key to FIG. 3:

C57B1/6 mice not treated with salbutamol=Δ

C57B1/6 mice treated with salbutamol (1.4 mg/l)=○

C57B1/6 mice treated with salbutamol (2.1 mg/l)=▲

These results show that the treatment with salbutamol significantly retards, in a dose-dependent manner, the appearance of the lethal effects of the anti-fas antibody.

What is claimed is:

1. A method of treatment of a patient in need of regulation of cellular apoptosis comprising administration of an effective amount of a β2-AR receptor modulator to a patient in need thereof.

2. The method of claim 1 wherein the β2-AR receptor modulator is a β-adrenergic agonist.

3. The method of claim 1 wherein the β2-AR receptor modulator is a β-adrenergic antagonist.

4. The method of claim 1 wherein the patient is in need of regulation of cellular apoptosis in hepatic cells.

5. The method of claim 4 wherein the patient is in need of inhibition of cellular apoptosis in hepatic cells.

6. The method of claim 4 wherein the patient is in need of activation of cellular apoptosis in hepatic cells.

* * * * *